United States Patent [19]

Abele et al.

[11] 4,235,244

[45] Nov. 25, 1980

[54] MICROBIOLOGICAL SPECIMEN SAMPLING DEVICE

[75] Inventors: John E. Abele, Concord; Robert G. Brown, Stow, both of Mass.

[73] Assignee: Medi-Tech, Incorporated, Watertown, Mass.

[21] Appl. No.: 928,702

[22] Filed: Jul. 27, 1978

[51] Int. Cl.$^3$ ............................................. A61B 10/00
[52] U.S. Cl. .................... 128/749; 128/756; 128/759; 73/421 B
[58] Field of Search .............. 128/749, 756, 759, 752, 128/772, 222, 304, 262, 269; 73/421 R, 421 B, 422 R, 423 A

[56] References Cited

U.S. PATENT DOCUMENTS

| | | | |
|---|---|---|---|
| 2,955,591 | 10/1960 | MacLean | 128/756 |
| 3,512,518 | 5/1970 | Mishkin et al. | 128/756 |
| 3,800,781 | 4/1974 | Zalucki | 128/749 |

OTHER PUBLICATIONS

Wimberley, et al., "A Fiberoptic Bronchoscopy Technique to Obtain Uncontaminated Lower Airways Secretions for Bacterial Culture", *American Review of Respiratory Disease,* vol. 119, Mar. 1979.

*Primary Examiner*—Willis Little
*Attorney, Agent, or Firm*—Wolf, Greenfield & Sacks

[57] ABSTRACT

A microbiological sampling device has inner and outer catheter tubes with a specimen sampling brush within the inner catheter body. A plug of water soluble material closes a distal end of the outer catheter body to prevent contamination of the inner catheter body and the brush during introduction into an organism, as for example, when placed in the lungs. The plug can be ejected and the sampling brush extended within the lungs to enable the brush to collect uncontaminated bacteria samples which are brushed into the inner body whereupon the entire assembly can be withdrawn. The plug protects the specimen sampling brush during introduction and is readily dissolvable avoiding unwanted biological problems, yet sealing the assembly against contamination.

21 Claims, 1 Drawing Figure

U.S. Patent      Nov. 25, 1980      4,235,244
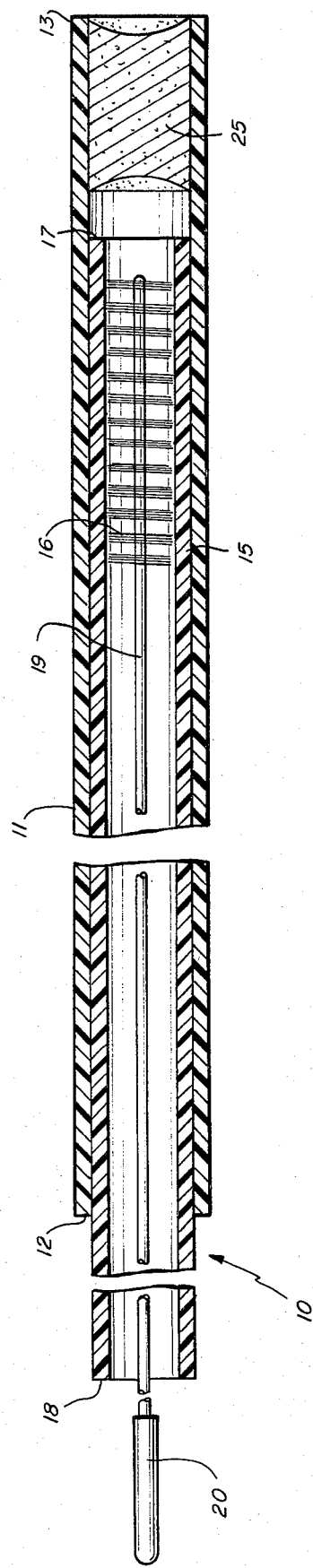

MICROBIOLOGICAL SPECIMEN SAMPLING DEVICE

BACKGROUND OF THE INVENTION

It has been difficult in the past to obtain uncontaminated bacteriological specimens from the lower respiratory track and other locations of the human body. There is a real need to be able to obtain ready access to lower airways to obtain specimens for culturing and determination of bacterial types. Fiber optic bronchoscopes are known for use in viewing of the lower airways of the lung, but sample collection through bronchoscopes often result in contamination of specimens taken, unless extraordinary precautions are taken.

In the past is has been proposed to use a single lumen catheter passed through the neck to the lower airways in transtracheal aspiration. Suction could then be applied to take a biological sample and the catheter withdrawn. This technique is often painful to the patient and requires a neck incision with problems of locating the catheter unless a bronchoscope is used.

In still another proposed method, a cytology brush is carried in a catheter plugged with a gel foam material to prevent contamination of the brush during introduction into the lower airway. The brush is then used to remove the plug and take a sample. The plug can cause a health problem when left in the lung. This method has not been found to be as effective as desired in that contamination by bacteria during passage through the upper respiratory areas can occur.

Sampling catheters of various types are found in the following U.S. patents and perhaps others: U.S. Pat. Nos.
2,767,703
2,839,049
2,955,591
3,613,664
3,800,781
3,877,464
3,881,464
4,023,559.

SUMMARY OF THE INVENTION

It is an object of this invention to provide a specimen sampling device for obtaining contamination-free bacterial specimens from within the body of an individual.

It is another object of this invention to provide a plug means for barring contamination of a sampling catheter carrying a collectoer, which plug can be disposed of within the body and is water soluble and physiologically safe.

It is still another object of this invention to provide an improved method of forming a plug on an end of a sampling catheter in accordance with this invention.

It is still another object of this invention to provide a method of using a sampling device in accordance with the preceding objects to obtain contamination-free bacterial specimens without leaving undesirable material after withdrawal from the body.

According to the invention a microbiological specimen sampling device for obtaining contamination-free specimens has a first outer catheter body or tube having a distal end and a proximal end. A second catheter body or tube extends axially within the first catheter body and also has a proximal end and distal end. A sample collector is contained within the second catheter body. A removable water soluble plug engages and seals a portion of the first catheter body toward the distal end thereof and is positioned between that distal end and the distal end of the second catheter body.

A means is provided for moving the two catheter bodies axial with respect to each other and a wire or other means extends through the inner catheter to the sample collector which is preferably a brush so that the sample collector can be pushed beyond the distal ends of both catheter bodies in use, collect the sample and bring the sample within the inner catheter body. The plug is preferably a water soluble wax-like material which is physiologically safe when disposed of in a body cavity such as the lungs. The wax-like or other plug material used preferably dissolves within a matter of minutes. It acts to seal the end of the catheter to prevent contamination of the brush and inner catheter during introduction into the body, yet is easily removable by movement of the inner catheter thereagainst and/or by pushing of the brush thereagainst. In some cases the sample collector need not be a brush but can be a vacuum which creates a suction and permits a sample to be drawn from a body cavity such as the stomach or other parts of the intestinal tract.

In the bronchial application, the double catheter body device with a cytology brush within the inner catheter and the end plugged with a water soluble wax is introduced through the trachea preferably by means of a bronchoscope. When in position in the lower passageways of the lung, the inner catheter is moved with respect to the outer catheter to release the plug where it drops into the lung and preferably dissolves within no more than ten minutes. The cytology brush is then moved outwardly and a bacteria sample collected whereupon the brush is used to withdraw the sample into the inner catheter which is then preferably moved with respect to the outer catheter so that the outer catheter extends beyond the distal end of the inner catheter. The entire device is then removed from the body.

Preferably the water soluble plug is positioned in the catheter end by melting the material of the plug and drawing it into the catheter end by capillary action. Should the plug later remelt as in sterilization it is unlikely to be displaced but will likely harden and reform in place.

It is a feature of this invention that substantially 100% reliability in collecting uncontaminated samples can be achieved. The device can be used through a bronchoscope to enable direct visual sampling. No surgery or incisions are required and no undesirable materials are left behind.

It is a feature of this invention that the biocompatible water soluble plug provides a germ-free seal and can be designed to have a reproducible amount of friction so that it doesn't fall out of the catheter too easily nor is it difficult to push out. The coaxial tube construction provides an extra level of contamination protection which is not obtainable in a single tube technique. The double catheter tubes can be made with a maximum outer diameter of the outer catheter tube of 1.8 millimeter which is small enough to be advanced through commercially available flexible bronchoscopes under direct vision. The entire assembly can be sterilized at standard sterilization conditions.

BRIEF DESCRIPTION OF THE DRAWINGS

The above and other objects, features and advantages of the present invention will be better understood from the following discussion when viewed in connection with the accompanying drawings where the single FIGURE shows a cross-sectional view through a coaxial double walled catheter construction of the present invention taken through the axis of the construction with an inner cytology brush shown in full. The preferred structure is specifically designed for use in a bronchial application.

DESCRIPTION OF THE PREFERRED EMBODIMENTS

With reference now to the drawing, the bronchial cytology sampling device 10 comprises a first outer catheter body or tube 11 which may be made of Teflon (polytetrafluoroethylene) or other conventional catheter material. The catheter preferably has an outside diameter no greater than about 1.8 millimeters so that it can slide easily within a bronchoscope. The catheter wall thickness of each tube is typically in the range of from 0.005" to 0.007" and the length may be from 90 cm to 100 cm, extending from the proximal end 12 to the distal end 13. A second or inner catheter body or tube 15 is preferably constructed of the same material as the outer tube and slidingly engaged therewith along the outer diameter thereof. The inner tube 15 slides within the lumen of the outer tube and carries a cytology collector 16 coaxially therein. The inner tube has a distal end 17 and a proximal end 18. A wire 19 connects the brush end 16 to a manipulating handle 20 which can be manipulated from outside a body.

A plug 25 is frictionally engaged between the distal ends 13 and 17 and seals the end 13 to prevent contamination during passage into the body. The material of the plug is biologically compatible with the human body and is preferably a water soluble wax or wax-like plug. Water soluble plugs useful in this invention include the plugs formed of polyethylene glycol such as polyethylene glycol having a molecular weight of from about 400 to 6000. The polyethylene glycol is preferably uniformly admixed with a material such as sugar to disrupt the crystal structure of the plug. A mixture of polyethylene glycol (molecular weight 4000) and 20% by weight of confectionery sugar (sucrose) has been found particularly beneficial for use as a plug in accordance with this invention. A mixture of 80% by weight polyethylene glycol (molecular weight 4000) and 20% by weight polyethylene glycol (molecular weight 400) has also been found to give excellent results when used as a plug material.

While the collector is preferably a brush, swabs and other collecting means known in the art may also be used. For example the brush, swab and the like can be completely eliminated and a vacuum can be used to draw a sample from a body cavity such as the stomach.

In use of the device, the entire device is passed through a bronchoscope into the lower lung. When the desired sampling site is reached, sputum and other contaminating secretions from the upper airway which may collect on the front end of the assembly is removed by advancing the inner Teflon tube thereby pushing out the plug and wiping the inner wall of the outer sheath or tube as well as the distal end thereof. The plug falls into the lung and preferably dissolves harmlessly within a few minutes as, for example, no more than ten minutes. The inner tube is advanced beyond the distal end of the outer tube and then the brush is advanced out and a sample of bacteria is raked into the inner tube. The entire assembly can be withdrawn preferably after first withdrawing the inner catheter slightly within the distal end of the outer catheter. This method provides for substantially 100% reliability. Various size samples can be collected depending upon the outer diameter of the outer tube which limits the overall construction.

In a specific example of this invention, a device 10 is constructed with the outer and inner tubes being formed of Teflon and being flexible with wall thicknesses of 0.006". The inner diameter of the outer catheter is 0.060" and the outer diameter of the inner catheter is 0.058". The inner diameter of the inner catheter is 0.044". The plug extends for an axial length of 5 mm and has an outer diameter such that it frictionally engages the inner diameter of the outer tube at the distal end. The polytetrafluoroethylene inner catheter carries a nylon bristle collector.

Unstimulated expectorated saliva is collected from volunteers and pooled in a beaker. The tip of a bronchoscope was placed into the saliva. The bronchoscope was then removed from the saliva and the test catheter was passed through the inner channel to a distance approximately six centimeters beyond the bronchoscope tip. The plug 25 was expelled by movement of the inner tube with respect to the outer tube and the brush was then advanced from the catheter tube into an 18-hour suspension containing $10^7$ CFR/ML of a neomycin-sensitive pigmented Serratia marcesens. After sampling the organism, the brush was retracted several centimeters into the catheter and the entire unit was removed from the bronchoscope. After removing the catheter from the bronchoscope, the distal portion was cleaned with 70% alcohol. It was then cut with a sterile scissors distal to the nylon brush 16. The brush was then advanced and cut off into a screw-capped glass vial containing 1 ml. of sterile saline. The vial was then vortexed vigorously. Serial one hundred fold dilutions of the sample were prepared to give final concentrations of $10^{-2}$, $10^{-4}$, and $10^{-6}$. Aliquots of 0.1 ml. of the undiluted specimen and the 3 serial dilutions were plated on 2 agar plate media. The first media contained 5% sheep's blood agar containing 100 u.g./ml neomycin sulfate and the second plate media contained MacConkey agar. The neomycin blood agar was known to inhibit the Serratia while allowing growth of common oral flora bacterial. The MacConkey agar was used to suppress the oral flora to permit accurate counts of Serratia. Quantitative cultures of the pooled saliva and broth culture of Serratia were performed to document the concentration of bacteria. The incidence and quantitation of contamination by salivary bacteria of the sampling brush is zero, as shown by the fact that there is growth on the MacConkey agar and no growth on the neomycin blood agar.

Generally the plug material of this invention has a reproducible stickiness so as to adhere to the inside of the tube end. Preferably it is easily applied. This is best done by a step in which it is melted and drawn into the tube by capillary action. For example, in the preferred embodiment, a polyethylene glycol material of 4000 molecular weight mixed with 20% by weight of confectionery sugar is melted at its melting temperature of about 150° F. and the end of the Teflon tube 13 is dipped in the melt to form a plug having a weight of about 80 milligrams. After removal from the melt, the plug hardens quickly. It is found that this method of forming the plug is simple, efficient and provides the correct degree of adherence of the plug to the inside wall of the catheter. In those cases where the catheter is of greater diameter than would permit capillary action, other methods of formation can be used. Where the polyethylene glycol material of the preferred embodiment is heated to gas sterilize as at temperatures of 150° F. or slightly above, melting does not cause displacement of the plug while allowing sterilization and reforming of the plug upon cooling. Thus gas sterilization at conventional temperatures of 140° can be carried out on catheters formed in accordance with the preferred embodiment without destroying the seal between the plug and the catheter.

Preferably the plug has reproducible stickiness or adherence to the interior of the tube as above described, can be easily applied, doesn't shrink during normal ambient temperatures and is biocompatible with the body and will dissolve in time periods preferably no longer than about ten minutes. The plugs used preferably range in weight from 5 to 100 milligrams.

While the preferred embodiment of the sampling device of the present invention is for bronchial use, the device can also be used for obtaining uncontaminated specimens from other specific parts of the body where a catheter must first pass through contaminated parts of the body. For example, the device could be used to obtain uncontaminated specimens from the stomach, the uterus and other body cavities. In some cases, the dimensions given will vary greatly where the device is to be used in other than bronchial areas. For example, stomach and uterus sampling devices can have larger dimensions than those given as preferable with respect to the bronchial area.

While a specific embodiment of this invention has been shown and described, it should be understood that many variations are possible. In all cases, a water soluble, biocompatible plug is used to provide protection against contamination during entrance of a sampling catheter device into the body with ease of removal of the plug and ease of collection of uncontaminated bacterial samples.

Although the catheters used are preferably cylindrical, tubular bodies of various cross-sectional designs can be used. Thus oblong, flattened and other cross-sectional shapes of the lumens as known in the art can be used. The plug is designed to plug the distal end no matter what the specific configuration of the lumen at the end. Similarly, although uniform wall catheter tubes are preferred, non-uniform wall tubes can be used as known in the art to increase rigidity at distal or proximal portions as may be desired and to enable ease of manipulation of the catheter to reach the desired body location.

What is claimed is:

1. A microbiological specimen sampling device for obtaining contamination-free specimens,
    said device comprising a first outer catheter body having a distal end and a proximal end,
    a second catheter body having a distal end,
    a sample collector contained within said second catheter body,
    a removable water soluble plug engaging and sealing a portion of said first catheter body toward said distal end in position between said distal end of said first catheter body and said distal end of said second catheter body,
    means for moving said first catheter axially with respect to said second catheter body and means for extending said sample collector beyond both said catheter body distal ends to permit said plug to be discharged and said sample collector advanced to obtain a sample.

2. A microbiological specimen sampling device in accordance with claim 1 wherein said sample collector is a brush.

3. A microbiological specimen sampling device in accordance with claim 1 wherein said water soluble plug is a polyethylene glycol material.

4. A microbiological specimen sampling device in accordance with claim 2 wherein said plug is formed of a polyethylene glycol material formed in place from a melt.

5. A microbiological specimen sampling device in accordance with claim 4 wherein said material has a weight of from 5 to 100 milligrams.

6. A microbiological specimen sampling device for obtaining contamination-free specimens,
    said device comprising a first outer catheter body having a distal end and a proximal end,
    a second catheter body having a distal end,
    a sample collector contained within said second catheter body,
    a removable plug engaging and sealing a portion of said first catheter body toward said distal end in position between said distal end of said first catheter body and said distal end of said second catheter body,
    means for moving said first catheter axially with respect to said second catheter body and means for extending said sample collector beyond both said catheter body distal ends to permit said plug to be discharged and said sample collector advanced to obtain a sample.

7. In a microbiological specimen sampling device for collecting bacterial specimens in a contamination-free manner,
    said device comprising a catheter having a distal end with a collector within that distal end, the improvement comprising a removable plug of a water soluble biocompatible material sealing said end against contamination when said distal end is introduced into the body of an individual.

8. The improvement of claim 7 wherein said water soluble biocompatible material is polyethylene glycol.

9. In a method of collecting bacterial samples without contamination,
    the process comprising selecting a double-tubed catheter having a collector within an inner tube with the inner and outer tubes each having distal ends coaxially arranged and axially spaced from each other,
    a plug of a water soluble biocompatible wax-like material plugging the distal end of said outer tube,
    introducing said device into a body cavity, moving said outer tube with respect to said inner tube to expel said plug into the body,
    moving said collector with respect to said device to enable said collector to collect a bacterial specimen,
    reversing movement thereof and bringing said specimen within said inner tube,
    and withdrawing said device from the body.

10. The method of claim 9 wherein said wax-like material is a polyethylene glycol.

11. A method in accordance with the method of claim 10 wherein said device is introduced into the lungs.

12. A method of forming a water soluble plug on an end of a catheter body, said method comprising, drawing a water soluble molten material into an end of said catheter and permitting said material to harden therein to form said plug, said plug being formed of a material which is biocompatible and dissolvable in the body.

13. A method in accordance with claim 12 wherein said catheter has an outer diameter of no more than about 1.8 millimeter.

14. A method in accordance with claim 13 wherein said water soluble plug has a weight of from 5 to 100 milligrams and is capable of dissolving in the body in no more than ten minutes at body temperature.

15. A method in accordance with the method of claim 14 wherein said water soluble plug is formed of a polyethylene glycol material.

16. A method in accordance with the method of claim 12 wherein said material once positioned in said catheter is not displaced by melting during sterilization of said catheter body.

17. A microbiological specimen sampling device for obtaining contamination-free specimens, said device comprising a first outer catheter body having a distal end and a proximal end, a second catheter body having a distal end, a removable water soluble plug engaging and sealing a portion of said first catheter body toward said distal end in position between said distal end of said first catheter body and said distal end of said second catheter body, means for moving said first catheter axially with respect to said second catheter body.

18. A microbiological specimen sampling device in accordance with claim 17 wherein said water soluble plug is a polyethylene glycol material.

19. A microbiological specimen sampling device in accordance with claim 17 wherein said plug is formed of a polyethylene glycol material formed in place from a melt.

20. A microbiological specimen sampling device in accordance with claim 17 wherein said material has a weight of from 5 to 100 milligrams.

21. In a microbiological specimen sampling device for collecting bacterial specimens in a contamination-free manner, said device comprising a catheter having a distal end, the improvement comprising a removable plug of a water soluble biocompatible material sealing said end against contamination when said distal end is introduced into the body of an individual.

* * * * *